United States Patent [19]

Lyon et al.

[11] Patent Number: 6,042,877
[45] Date of Patent: Mar. 28, 2000

[54] METHOD FOR THE MANUFACTURE OF ANTI-MICROBIAL ARTICLES

[75] Inventors: Keith R. Lyon, Hudson, Wis.; Michael M. Rock, Jr., Oakdale, Minn.

[73] Assignee: 3M Innovative Properties Company, St. Paul, Minn.

[21] Appl. No.: 09/123,660

[22] Filed: Jul. 28, 1998

[51] Int. Cl.[7] .............................. A61L 15/00; B05D 1/40; B05D 3/00; B05D 3/04; B05D 3/10

[52] U.S. Cl. ...................... 427/2.31; 427/331; 427/333; 427/337; 427/340; 427/342; 427/402; 424/405; 424/409; 424/411; 424/443; 424/617; 424/630; 424/641; 424/646; 514/55; 514/65; 514/365; 514/372; 514/396; 514/401; 514/507

[58] Field of Search .................................. 427/2.31, 331, 427/333, 337, 340, 342, 402; 424/405, 409, 411, 443, 617, 630, 641, 646; 514/55, 65, 365, 372, 507, 396, 401

[56] References Cited

U.S. PATENT DOCUMENTS

| | | | |
|---|---|---|---|
| 2,958,593 | 11/1960 | Hoover et al. | 51/295 |
| 3,940,482 | 2/1976 | Grand | 424/245 |
| 4,991,362 | 2/1991 | Heyer et al. | 51/400 |
| 5,025,596 | 6/1991 | Heyer et al. | 51/400 |
| 5,282,900 | 2/1994 | McDonnell et al. | 134/2 |
| 5,308,673 | 5/1994 | Tochacek et al. | 428/102 |
| 5,541,233 | 7/1996 | Roenigk | 521/54 |
| 5,585,407 | 12/1996 | Patel et al. | 514/772.6 |
| 5,614,538 | 3/1997 | Nelson, Jr. | 514/345 |
| 5,641,563 | 6/1997 | Truong et al. | 442/327 |
| 5,643,971 | 7/1997 | Roenigk | 523/122 |

FOREIGN PATENT DOCUMENTS

| | | |
|---|---|---|
| 8-13341 | 1/1996 | Japan . |
| 8-27675 | 1/1996 | Japan . |
| 8-134778 | 5/1996 | Japan . |

*Primary Examiner*—Nathan M. Nutter
*Attorney, Agent, or Firm*—Michaele A. Hakamaki

[57] ABSTRACT

A method for making an anti-microbial article is described, the method comprising: providing a substrate; forming a solution comprising a chelating polymer and a metal ion; depositing the solution on the substrate; drying the substrate to form a coated substrate; and adding a potentiator to the coated substrate to form the antimicrobial article. Forming of the solution comprises (A) selecting a chelating polymer from the group consisting of polyglucosamines, ethylene acrylic acid copolymers, polycarboxylic acids, and polyamines, (B) dissolving the chelating polymer in acid to form an acidic solution, (C) preparing an aqueous solution of the metal ion, preferably by selecting a salt of the metal ion and dissolving the salt in water, and (D) combining the aqueous solution of the metal ion and the acidic solution. The addition of the potentiator to the coated substrate is accomplished by dissolving the potentiator in water to provide a potentiator solution, treating the coated substrate with the potentiator solution, drying the substrate to provide the finished anti-microbial article. The invention provides a method for the treatment of any of a variety of substrates to thereby render the substrate resistant to certain microbial growth.

18 Claims, No Drawings

METHOD FOR THE MANUFACTURE OF ANTI-MICROBIAL ARTICLES

This invention relates to a method for the manufacture of articles resistant to microbial growth and to a method for the treatment of a substrate to impart anti-microbial properties to the treated substrate.

BACKGROUND OF THE INVENTION

The control of mold, mildew, algae, fungi, and other microbes or microorganisms in moist or humid environments has long been a matter of concern. Biocides such as mildewcide, anti-microbial, antiseptic, disinfectant, sanitizer, germicide, algaecide, slimicide, antifouling agent, or preservative are typically employed to remove microbes from an area and prevent their recurrence.

Absorbent articles used for cleaning (e.g., sponges and wiping articles) can harbor microorganisms such as bacteria and fungi that thrive and rapidly multiply in moist environments. In the food service and medical industries, sanitation and prevention of the spread of infections is of the utmost importance. Consequently, it is desirable to use materials which will control or prevent the growth of unwanted microorganisms. Various approaches have been taken to the problem of microbial growth in articles such as sponges and other wiping and cleaning articles, for example. Cellulose sponges treated with germicides and biocides, including alkali metal salts in combination with quaternary ammonium compounds as well as alkali metal montmorillonite clays, have been used with some success. Metal dialkyl dithiocarbamates have also been used as biocides in pigmented sponges. The sponges prepared by these methods, although initially effective, generally do not have long-lasting antimicrobial activity because the biocides tend to wash out of sponges upon rinsing with water or when the article is used in cleaning applications.

One approach to introducing a long-lasting anti-microbial agent into an absorbent sponge is described in U.S. Pat. No. 5,541,233 (Roenigk). Durable, long-lasting anti-microbial sponges are formed by mixing a metal ion and a dispersion of a chelating polymer with the viscose cellulose used to make the sponge, followed by treatment with heat or acid which causes coagulation and regeneration into a sponge. The sponge is rinsed, leaving a porous structure having the chelating polymer in it. This is followed by the addition of a potentiator (i.e., an antimicrobial agent) which is believed to react with the metal ion.

However, a need exists for methods of making durable long-lasting anti-microbial articles which do not require regeneration or further processing of the final article.

SUMMARY OF THE INVENTION

This invention provides a method of making antimicrobial articles. These articles provide long lasting protection from the growth of a variety of microbes such as mold, mildew, algae, fungi, and the like.

In one aspect, the invention is a method of making an anti-microbial article comprising:
  providing a substrate;
  forming a solution comprising a chelating polymer and a metal ion;
  depositing the solution on the substrate;
  drying the substrate to form a coated substrate; and
  adding a potentiator to the coated substrate to form the antimicrobial article.

The forming of the solution comprises (A) selecting a chelating polymer from the group consisting of polyglucosamines, ethylene acrylic acid copolymers, polycarboxylic acids, and polyamines, (B) dissolving the chelating polymer in acid to form an acidic solution, (C) preparing an aqueous solution of the metal ion, preferably by selecting a salt of the metal ion and dissolving the salt in water, and (D) combining the aqueous solution of the metal ion and the acidic solution. A particularly preferred polyglucosamine is chitosan. The metal ion is preferably selected from the group consisting of zinc, zirconium, iron and copper.

In depositing the solution onto a substrate, a variety of methods are suitable such as dipping the substrate in the solution and wringing excess solution from the substrate after dipping. The addition of the potentiator to the coated substrate is accomplished by dissolving the potentiator in water to provide a potentiator solution, treating the coated substrate with the potentiator solution, drying the substrate to provide the finished anti-microbial article. The potentiator may be selected from the group of alkyl dithiocarbamates, thiazoles, imidazoles, pyrithione or mixtures thereof.

The invention provides a method for the treatment of any of a variety of substrates to thereby render the substrate resistant to certain microbial growth, as evidences in the test results set forth in the Examples herein. By way of example, the invention provides a method for the application of a preferred antimicrobial complex to any of a variety of substrates. In particular, a complex of a chitosan-based antimicrobial complex may be applied to such substrates for the purpose of rendering the substrate highly resistant to microbial growth such as fungal growth and the like. In particular, a chitosan—metal- pyrithione complex may be readily applied to virtually any substrate surface to provide a finished article suitable for cleaning applications and the like with antimicrobial properties that will withstand repeated uses of the article even after significant water exposure.

Those skilled in the art will further appreciate the utility, novelty and nonobviousness of the present invention upon consideration of the remainder of the disclosure including the detailed description of the preferred embodiment, the examples herein and the appended claims.

DETAILED DESCRIPTION OF THE PREFERRED EMBODIMENTS

In this invention, a solution of a metal ion and a chelating polymer is prepared and deposited onto a substrate. After the substrate is dried, a solution containing a potentiator is added to impart long-lasting anti-microbial characteristics to the substrate. The anti-microbial article is useful in certain cleaning applications (e.g., as a sponge or a scouring pad), or any application where anti-microbial characteristics would be beneficial.

Metal ions suitable for use in this invention are capable of forming bonds (e.g., coordinate covalent bonds) with molecules generally referred to as ligands or chelating agents. Suitable metals include transition metals (i.e., groups IB—VIIIB of the periodic table of elements) available as water-soluble salts. In addition, main group metals capable of forming a complex with the chelating polymer of this invention may also be suitable. Useful metal ions include $Zn^{+2}$, $Zr^{+2}$, $Fe^{+2}$ $Cu^{+2}$. Such metal ions are available as water-soluble salts, that is, for example, acetate, chloride, and sulfate salts of the metals including hydrates thereof. Based on commercial availability and the relatively low cost of water-soluble salts of zinc, a preferred metal ion is $Zn^{+2}$. Preferred zinc salts include zinc acetate and zinc chloride.

In solution, the metal ion forms a complex with the chelating polymer. Chelating polymers suitable for use in this invention preferably are capable of forming a film when coated on a surface. Suitable polymers include polyglucosamine, ethylene acrylic acid copolymer, polycarboxylic acid, alkyleneimines and polyamine, for example. A preferred chelating polymer is a polyglucosamine also referred to as chitosan, the deacetylated derivative of the polysaccharide chitin ($\beta$-(1,4)-poly-N-acetyl-D glucosamine) and an abundant natural by-product of the shrimp and crab industries.

In the method of this invention, the chelating polymer is dissolved in a suitable solvent, including water as well as polar organic solvents such as alcohols and ketones. Water is the preferred solvent. In dissolving the chelating polymer, it may be desirable to add sufficient acid (e.g., acetic acid) or base (e.g., NaOH) to facilitate dissolution of the polymer and assist in producing a homogeneous solution. When the chelating polymer is chitosan, sufficient acid is added to provide an acidic pH so that the acid protonates the amine groups on the chitosan to thereby solubilize it into solution. Typically, a solution having a pH of about 6 or less is sufficient to dissolve the chitosan. Suitable acids for use in dissolving the chitosan include organic and inorganic acids. Without limitation, suitable organic acids include acetic, adipic, formic, lactic, malic, malonic, propionic, pyruvic, and succinic. Suitable inorganic acids include hydrochloric and nitric, for example.

The chelating polymer, and any added acid or base, is dissolved into solution typically by stirring for a sufficient time, (e.g., several minutes). Metal ion is then added to the polymer solution, either as a solid salt or as a solution of the metal salt. A convenient technique for adding the metal ion to the solution is to first make a dilute solution of the metal salt in the desired solvent and add it with stirring to an equal amount of a dilute solution of the chelating polymer. This resulting ion/polymer solution may then be applied to a substrate.

Additives optionally may be included in the ion/polymer solution. For example, one or more pigments, pigment fixing agents, processing aids (e.g., wetting agent, defoamer, viscosity reducer, thickener), adhesion promoters, antioxidants and the like can be added to the ion/polymer solution before it is applied to a substrate. Pigment may be used in the ion/polymer solution to match the color of the coating to that of the substrate, or possibly as a color-coded identification aid for the finished anti-microbial product. Immobilizing agents in the ion/polymer solution immobilize the chelated polymer on the substrate. A suitable immobilizing agent is epoxysilane. Other such immobilizing agents may also be used such as aziridine or other known cross-linking agents. Without being bound to any particular theory, the crosslinking agent or the immobilizing agent will react with the hydoxyl groups on the chitosan and the substrate to further bind the antimicrobial agent to the substrate. A preferred additive for the ion/polymer solution is 3-(trimethoxysilo) propylglycidylether (commercially available under the trade designation A- 187 from OSi Specialties Inc., Danbury, Conn.).

It is contemplated that the ion/polymer solution can also be mixed with a coatable binder of the type normally used in the manufacture of the finished article. For example, in the manufacture of nonwoven articles, a binder is typically required to bond the fibers thereof to one another at their points of intersection and/or contact and to maintain the finished articles in a preferred configuration. Preferably, the binder will be miscible with the ion/polymer solution.

Where the foregoing binder is a component of the finished product, the ion/polymer solution of the invention may be introduced into the manufacturing process with the binder in the same process step. Suitable binders compatible with the ion/polymer solution of the invention include water-soluble binders such as polyvinylalcohol (PVA), and dispersions or latices of acrylics or phenolics, for example. Even if the finished article normally would not require the use of a binder, the ion/polymer solution may be mixed with such a binder in order to improve the adhesion of the metal ion/ chelating polymer to a substrate. Those skilled in the art will appreciate that the ratio of ion/polymer solution to binder will likely vary with the specific application. Hence, the relative amounts of the ion/polymer solution and the binder will be determined empirically in accordance with the nature of the article being manufactured and its intended use.

The ion/polymer solution can be applied to a substrate by any of a variety of known coating methods, including spraying, knife coating, roll coating, spin coating, immersion coating, and the like. The coating method chosen for the manufacture of a particular article may depend on the form of the substrate as well as other factors known to those skilled in the art. It is generally desirable to have the ion/polymer solution deposited over the entire available surface of the substrate, but this is not essential. The desired amount of coating depends upon the type and application for a particular substrate. Typically, a minimum level of potentiator is about 30 ppm based on the sensitivity of current analytical methods. Lower levels of the potentiator may continue to be effective in certain applications against certain bacteria. More preferably, the potentiator level is between 1500 to 3000 ppm based on the total weight in grams of the dried substrate. Below the 1500 ppm level, the effectiveness of the antimicrobial article might be compromised against certain fungi, as determined by the ASTM Fungal Challenge set forth in the Examples below.

After the ion/polymer solution is deposited onto the substrate, the coated substrate is dried at room temperature or at elevated temperatures for a time sufficient to remove the solvent. Preferably, drying is accomplished by heating using a conventional drying oven operated at temperatures from about 105° C. to about 120° C. are sufficient to drive off the solvent, dry the chelated polymer and form a suitable file over the treated substrate. At temperatures above 120° C., some discoloration of the chelated polymer can occur. At temperatures below 105° C., the drying rate can be undesirably slow.

If a binder has been used in the manufacture of the article, the ion/polymer solution may have been mixed with the binder or applied over the binder. In any event, a heat treatment is typically needed to cure the binder. In this case, the temperatures may range up to about 150° C., depending on the type of binder and the thickness of the substrate. In this case, it may be preferable to use a substrate of a darker color to mask the aforementioned discoloration.

After the article is dried, it is preferably treated with another solution containing a potentiator. "Potentiator'" as used herein refers to an anti-microbial agent capable of bonding to the metal ion. It should be noted that the selection of potentiator is dependent upon the coordination chemistry of the metal ion. For example, if the bonds between the chelating polymer and the metal ion can be completely displaced by a potentiator, the durability of the complex within the chelating polymer can be compromised. Thus, the use of such a potentiator would not be desirable. The potentiator solution may be applied by known coating methods such as those mentioned above for the application of the ion/polymer solution. To maximize the anti-microbial activity of an article prepared by this method, the entire available surface of the coated substrate is preferably exposed to the potentiator solution. However, a desired level of anti-microbial activity may be achieved without coating the entire available surface.

Suitable potentiators include, but are not limited to, alkyl dithiocarbamates, thiazoles, imidazoles, pyrithiones, and mixtures of these. Suitable alkyl dithiocarbamates include those wherein each alkyl group of the carbamate has up to about eight carbons. The alkyl groups can be straight or branched. Representative dithiocarbamates include dimethyl dithiocarbamate, diethyl dithiocarbamate, dipropyl dithiocarbamate, dibutyl dithiocarbamate, methyl ethyl dithiocarbamate, methyl propyl dithiocarbamate, methyl butyl dithiocarbamate, dihexyl dithiocarbamate, dioctyl dithiocarbamate, and the like. A preferred alkyl dithiocarbamate is dimethyl dithiocarbamate, commercially available under the trade designation "Vancide 51" from R. T. Vanderbilt of Norwalk, Conn. Imidazole is a five-membered heterocycle containing one N-H group and one unsaturated nitrogen. An example of a suitable substituted imidazole is 2-(4-thiazolyl)benzimidazole. Thiazoles are five-membered rings containing nitrogen and sulfur. An example of a suitable thiazole is 2-mercaptobenzothiazole. 2-mercaptobenzothiazole is available under the trade designation "Captax" from R. T. Vanderbilt. A particularly preferred potentiator is 1-hydroxy-2(1H)-pyridinethione, referred to in the art as both pyridinethione and pyrithione. Pyrithiones are typically sold as sodium salts and are commercially available, for example, under the trade designation "OMADINE" from Olin Corporation of Cheshire, Connecticut in 40% aqueous solutions. The potentiator is applied to the substrate in an amount sufficient to produce an anti-microbial effect in the finished article, as is exemplified herein.

Many types of substrates are suitable for use in this invention. Preferably, substrates are those considered useful in applications where anti-microbial activity is advantageous. This includes filtration applications such as a vacuum cleaner bag, a furnace filter, and respiratory masks. Personal products such as hair or make-up brushes made of naural or synthetic bristles as well as body sponges may also be manufactured or treated according to the invention. It may be desirable to make anti-microbial plastic sheeting (e.g., polyvinylchloride (PVC) films) according to the method of the invention. Cleaning, scrubbing, or wiping articles are well suited for manufacture according to the method of the present invention. Such articles include brushes, mops, brooms as well as smaller wiping articles such as sponges, non-woven webs or mats, paper articles, and conventional woven textiles such as towels, dishcloths, and bibs. The substrate may be non-absorbent, such as are useful in abrasive-containing pads (e.g., scouring pad and polishing pads). The substrates may comprise any of a variety of natural or synthetic materials. A particularly useful substrate shape is a fiber made of natural and/or synthetic materials and articles made with such fibers. Suitable natural fibers include cotton, flax, hemp, ramie, rayon, burlap, shoddy cotton, cotton linters, and pulp fibers. Suitable synthetic fibers include viscose rayon, cuprammonium rayon and the like, polyolefin fibers such as polyester, polypropylene, and polyamide fibers, polyvinyl alcohol, nylon and acrylic fibers. Polymeric foams such as polyurethane foams can be used as the substrate in the process of the invention.

Nonwoven webs are particularly useful as substrates because of their utility in the manufacture of cleaning and/or scouring articles. Nonwoven webs may be absorbent (such as those used in wiping articles) or non-absorbent (such as those used in scouring or polishing applications). Nonwoven webs used for scouring or polishing applications may contain abrasive particles. Suitable nonwoven webs may be made of an air-laid, carded, stitch-bonded, spunbonded, wet laid, or melt blown construction. A typical nonwoven web is characterized by being open, lofty, three-dimensional air-laid nonwoven substrate such as are described by Hoover et al. in U.S. Pat. No. 2,958,593, incorporated herein by reference. Also, the nonwoven web can be a low density nonwoven article formed of a multiplicity of crimped filaments (e.g., thermoplastic filaments) wherein one end of substantially all of the filaments are bonded together at a first bonding site and a second end of substantially all of the filaments are bonded together at a second bonding site with a nonbonded portion of the filament array in between the first and second bonding sites. Such a nonwoven web is described in U.S. Pat. Nos. 4,991,362 and 5,025,596, both to Heyer et al., the disclosures of which are incorporated herein by reference.

The nonwoven web preferably comprises a first major web surface, a second major web surface, and a middle web portion extending between the first and second major web surfaces. The web is made of a suitable synthetic fiber capable of withstanding the temperatures at which impregnating resins and adhesive binders are cured without deterioration. Useful nonwoven webs preferably have a weight per unit area at least about 50 g/m$^2$, and may range up to 200 g/m$^2$.

Nonwoven webs may be reinforced and consolidated by methods that entangle the fibers. These methods include needle tacking, hydroentangling, and the like. Nonwoven webs may also be reinforced by stitchbonding or other conventional textile methods. Stitchbonding is a method of bonding at least two fabrics or at least two layers of the same fabric together. The method is useful in increasing the thickness of nonwoven webs and tends to increase their durability. The fibers of the nonwoven are typically bonded to one another at their points of intersection and/or contact by use of a binder. Suitable binders include resinous adhesives, for example, such as a thermosetting water-based phenolic resin. Melt-bondable fibers can be used in the nonwoven web either alone or in combination with the foregoing adhesives. When exposed to high temperatures, the melt-bondable fibers will soften and/or melt and, upon cooling, adhere to other fibers in the web.

Nonwoven fibrous substrates of this type also may contain abrasive particles. Typically the particles are mixed with a binder and applied to the nonwoven web. Alternatively, the abrasive particles could be applied to the surface of a molten binder or a binder made tacky by application of heat, for example. Abrasive particles can be characterized as hard abrasive, soft inorganic abrasive, or plastic abrasive particles. Conventional hard abrasive particles include aluminum oxide; metal carbides, borides, and nitrides; fused alumina zirconia; and sol gel abrasive particles, as well as minerals such as diamond and garnet. Conventional soft inorganic abrasive particles include silica, iron oxide, chromia, ceria, zirconia, titania, silicates and tin oxide as well as metal carbonates, metal sulfates, aluminum trihydrate, graphite, and metal particles. Plastic abrasive particles can be formed from thermoplastic materials as well as therosetting materials such as polyvinyl chloride or melamine-formaldehyde resin, respectively. The nonwoven web may be coated with a mixture of two or more different abrasive particles. The abrasive particle can be treated to improve the adhesion between the abrasive particle and the binder.

The nonwoven webs can further comprise additives such as surface modification additives, curing agents, coupling agents, plasticizers, fillers, expanding agents, fibers, antistatic agents, initiators, suspending agents, photosensitizers, lubricants, wetting agents, surfactants, pigments, dyes, UV stabilizers and suspending agents. These materials may be useful depending upon the presence of a binder in the nonwoven web and/or depending upon the use of the web. Those skilled in the art will appreciate that nonwoven articles can be made in various configurations and constructions and using any of a variety of materials and ingredients. In general, the method of the invention is capable of treating all such embodiments.

One nonwoven article for use as a substrate in the practice of the invention is that described in U.S. Pat. No. 5,282,900 (McDonell, et al.), incorporated herein by reference. The article comprises an open, lofty, three-dimensional nonwoven web comprising a plurality of thermoplastic organic fibers, a binder which adheres the fibers at points of mutual contact, and abrasive particles bonded to the fibers by the binder. The abrasive particles range in size from about 0.1 to about 30 micrometers.

Another preferred substrate for use in the method of this invention is a nonwoven web comprising hydrophilic fibers and a binder comprising a crosslinked polyvinyl alcohol (PVA). Such a substrate is disclosed in U.S. Pat. No. 5,641,563 (Truong et al.), incorporated herein by reference. Preferred hydrophilic fibers include the following fiber types: cellulosic-type fibers such as PVA (including hydrolyzed copolymers of vinyl esters, particularly hydrolyzed copolymers of vinyl acetate), cotton, viscose rayon, cuprammonium rayon and the like; as well as thermoplastics such as polyesters, polypropylene, polyethylene, nylons and the like. Preferred cellulosic-type fibers for absorbent wiping articles are rayon and polyvinyl alcohol (PVA) which are commercially available as staple fibers.

Other useful substrates include woven and knitted materials as well as sponges and sponge cloth. Synthetic sponges typically are comprised of viscose cellulose, and may also contain reinforcing fibers. The viscose cellulose can be made from any conventional viscose technique. The viscose cellulose is commonly prepared through the mercerization and shredding of wood pulp, followed by xanthation with carbon disulfide, dilution with water, and finally, mixing the mixture. After the viscose cellulose is made, crystals of sodium sulfate decahydrate, referred to as Glauber's Salt, are added to the viscose cellulose. Reinforcing fibers or other additives are then added. The resulting mixture is heated to about 100° C., causing the cellulose to coagulate while melting the sodium sulfate. The sodium sulfate is rinsed from the resultant regenerated sponge leaving a porous structure. Woven and knitted materials include, for example, bath towels, dish cloths and the like.

PREPARATIVE PROCEDURES

In the Examples set forth below, the following preparative procedures were employed.

PROCEDURE A—ION/POLYMER SOLUTION 10 grams of glacial acetic acid were added to 480 grams of water and placed under a mixer. 10 grams of Chitosan (obtained from Vanson Chemical Company of Redmond, Washington) was weighed out and added to the already agitated solution of acetic acid with adequate stirring until the polymer was dissolved. A zinc acetate solution was prepared by dissolving 10 grams of zinc acetate dihydrate, (Aldrich Chemical Company) in 490 grams of water. The chitosan and the zinc acetate solutions were then combined under continuous mixing to provide an ion/polymer solution suitable for the manufacture of anti-microbial articles.

In some of the Examples, cupric sulfate pentahydrate or iron (II) sulfate heptahydrate (both from Aldrich Chemical Companies, Milwaukee, Wis.) were substituted for the zinc acetate dihydrate in the formulation of the ion/polymer solution. In all other respects, the ion/polymer solutions comprising the iron or copper ions were made identically to the above zinc solution. The weight percent zinc used in the ion/polymer mixture was 0.298% zinc by weight (1.0% zinc acetate dihydrate). An equivalent amount of iron (II) sulfate heptahydrate in 1 liter of ion/polymer solution was 14.82 grams (0.298% Fe). Likewise, an equivalent amount of cupric sulfate pentahydrate was 11.70 grams in 1 liter of ion/polymer solution, providing 0.298% copper in solution.

PROCEDURE B—ANTI-MICROBIAL SOLUTION

A commercially available sodium pyrithione solution (Olin Chemical Company, Stanford, Connecticut), 40% by weight was diluted down to obtain a pyrithione concentration of 3000 ppm adding 7.5 grams of the commercial solution to 1992.5 grams of water. This resulting solution was stirred thoroughly.

PROCEDURE C—TREATMENT OF SUBSTRATES

Substrates were soaked in the Ion/Polymer Solution for approximately one minute, removed and wrung out using a zero clearance wringer. The coated substrates were placed in an oven maintained at about 113° C. (235° F.) until they were thoroughly dried. The thus treated and dried substrates were submersed in the pyrithione Anti-Microbial Solution for one hour. After the one hour submersion, excess unreacted pyrithione was removed from the substrates by rinsing each substrate in water and passing it through a zero clearance wringer. The rinsing and subsequent wringing of each substrate was repeated 10 times. The rinsed substrates were dried in the oven overnight at 60° C. and tested for attached pyrithione by reacting the pyrithione with an iron chloride reagent and analyzing the substrate by absorption spectrometry (Beckman DU 640 Spectrophotometer purchased through Beckman Instruments Inc. in Fullerton, Calif.).

TEST METHODS AND MATERIALS

Articles made in the Examples below were evaluated according to the following methodology.

Bacterial Kill Assay

Substrates were tested for anti-microbial activity by measuring their effectiveness against certain bacterium. The test substrates were subjected to a water rinsing protocol to allow an evaluation of the durability of the antimicrobial treatment for the substrate. The rinsing protocol consisted of saturating the substrate in running tap water maintained at about 130° F. (54° C.) and thereafter wringing the saturated substrate, with the rinsing/wringing cycle being repeated as many as 400 times per sample. Prior to performing the kill assay, some of the samples were autoclaved for 30 minutes at 121° C. to reduce possible bacterial contamination introduced by the rinsing protocol. The thus prepared substrate samples were placed in sterile sample bags (available under the trade designation "Tekmar" from VWR Scientific of Philadelphia, Pa.) for a bacterial assay.

A bulk inoculum containing approximately $1\times10^6$ colony forming units (cfu)/ml was prepared in peptone water using *salmonella choleraesuis subsp. choleraesuis serotype typhimurium* (ATCC 14028). Each substrate sample was inoculated with 20 ml of the bulk suspension and placed in a Model 80 Stomacher Lab Blender (obtainable from VWR Scientific of Phildelphia, Pa.) for two minutes on high (260 rpm) to distribute the organisms throughout the substrate. Viable organisms were enumerated by removing 1 ml of solution from the sample bag and performing a 10-fold serial dilution in peptone water. One ml from each test tube used in the serial dilution , along with 1 ml of sample from the sterile sample bag, were pour plated in duplicate using trypticase soy broth agar (TSBA). The plates were incubated for two to three days at 28° C. and then examined for microbial growth. Each of the substrates was sampled immediately after inoculation and at 1 day, 3 days, and 7 days post-inoculation. A separate set of substrates was also tested as above using a mixed suspension of *Pseudomonas chlororaphis* (CRL ID #3357) and *Pseudomonas putida* (CRL ID #3352).

Fungal Challenge Test

Substrates were prepared as in the Bacterial Kill Assay starting with the rinse step described therein. The substrates were then tested in accordance with standardized test method ASTM G21-90 by aerosolizing a mixed fungal spore suspension of known concentration onto the sample surface and incubating the material at 28° C./95% relative humidity for 28 days. Samples are aseptically placed onto the surface of a minimal salts (M-9) agar plate and inoculated. The media used did not contain a carbon source. Therefore, fungal growth indicated a breakdown of sample components. The standard test uses five organisms: *Aspergillus niger* (ATCC 9642), *Penicillium pinophilum* (ATCC 11797), *Chaetomium globosum* (ATCC 6205), *Gliocladium virens* (ATCC 9645) and *Aureobasidium pullulans* (ATCC 15233). In addition, a separate set of samples was prepared as above and inoculated using a species of Penicillium characterized in part by its apparent immunity to the chitosanzinc-pyrithione complex. Samples were examined daily for the presence of fungal growth and the level of growth was rated at certain intervals, as indicated herein. A piece of sterile filter paper served as a positive control.

EXAMPLES

The following non-limiting Examples further illustrate aspects of the invention. Unless otherwise indicated, all parts and percentages are by weight.

Example 1

Nonwoven wipes commercially available under the trade designation "O-Cel-O All-Purpose Wipes" from Minnesota Mining and Manufacturing Company, St. Paul Minn. were prepared according to Preparative Procedures A-C using zinc/chitosan as the ion/polymer solution and pyrithione as the antimicrobial.

Example 2

Anti-microbial articles were prepared using sponge cloth commercially obtained from Kalle Nalo GmbH of Wiesbaden, Germany. The articles were prepared according to the above described Preparative Procedures A-C except that the ion/polymer solution was prepared to include 0.6% by weight zinc acetate dihydrate and 0.6% by weight chitosan along with 1.0% 3-(trimethoxysilo) propylglycidylether (commercially available under the trade designation "A-187" from OSi Specialties Inc., Danbury, Conn.).

Example 3

Anti-microbial articles were prepared using sponge cloth commercially obtained from Kalle Nalo GmbH of Wiesbaden, Germany. The articles were prepared according to the above described Preparative Procedures A-C except that the Ion/Polymer Solution was 1.0% polyethyleneimine (PEI) (available from Hoechst Celanese of Portsmouth, Va. under the designation "Corcat P-12") as the chelating polymer with 1.0% zinc and 1.0% 3-(trimethoxysilo) propylglycidylether. The substrates were treated with sodium pyrithione solution having a concentration of 1000 ppm in 1 liter.

Example 4

Anti-microbial articles were prepared using a sponge cloth available through Spontex Company (Columbia, Tenn.) as the substrate. The substrates were treated as in Example 2 except that the Ion/Polymer Solution was at 0.5 wt % for each of the components.

Example 5

Cellulose sponges commercially available from Minnesota Mining and Manufacturing Company, St. Paul Minn. under the trade designation "Niagara" were treated as in Example 2 except the percent by weight of the chitosan and the zinc acetate dihydrate in the Ion/Polymer Solution was 0.5%.

Example 6

Cellulose sponges ("Niagara" sponges from Minnesota Mining and Manufacturing Company, St. Paul Minn.) were treated as in Example 5 except the Ion/Polymer Solution included 0.5% 3-(trimethoxysilo) propylglycidylether.

Example 7

A series of substrate were treated according to the above Preparative Procedures A–C to illustrate the variety of possible substrates that can be treated by the anti-microbial treatment of the invention. The treated substrates were: (1) Polyurethane Sponges, from the Dayton Hudson Corporation, Minneapolis, Minn.; (2) Terrycloth Towels, also from Dayton Hudson Corporation; (3) Loofah Sponge, available under the trade designation "L'Esprit" , Sunny Marketing Systems Incorporated, Port Washington, N.Y.; (4) Wipes available under the trade designation "Handi Scrub Cloth", from Kimberly-Clark, Neenah, Wis.; and (5) a microfiber containing wipe commercially available under the trade designation "3M High Performance Cloth" from Minnesota Mining and Manufacturing Company, St. Paul Minn.

Example 8

Cellulose sponges were treated according to the Preparative Procedures A–C using copper as the chelating ion in the Ion/Polymer Solution. The thus treated sponges turned dark black due to the reaction of the copper with the sodium pyrithione.

Example 9

Cellulose sponges were treated according to the Preparative Procedures A–C using iron as the chelating ion in the Ion/Polymer Solution. The thus treated sponges turned dark black from the reaction of the iron with the sodium pyrithione.

Comparative Example A

Untreated sponge cloth commercially obtained from Kalle Nalo GmbH of Wiesbaden, Germany was used as a comparative example in the antimicrobial testing set forth herein.

Comparative Example B

Untreated sponge cloth obtained from Spontex Company of Columbia, Tenn. was used as a control for the comparative testing set forth herein.

Comparative Example C

An untreated non-woven wipe product commercially available from Colgate-Palmolive Company under the trade designation "Handi Wipe" was used as a control in the comparative testing set forth herein.

Comparative Example D

A non-woven wiping product obtained from Novapharm Research (Australia) Pty Ltd. was used as a control. This wiping product is purchased as an anti-microbial and is believed to include zinc pyrithione as an antimicrobial agent.

Examples 2 And 4 And Comparative Examples A And B

Articles made according to Examples 2 and 3 were tested by the Bacterial Kill Assay and the Fungal Challenge Test described above. Data for the Bacterial Kill Test is set forth for the organisms of Salmonella and Pseudomonas in Tables 1 and 2, respectively. Data for Pseudomonas is set forth in Table 2.

Results of the Fungal Challenge Test are shown in Table 3.

Additionally, samples were treated with a strain of Penicillium normally immune to the anti-microbial effects of the zinc-pyrithione complex. This was conducted as a control, with the expectation that the Penicillium test would show failure for all samples tested, including the samples prepared according to the invention. Results of the fungal challenge with Penicillium are set forth in Table 4.

Example 1 And Comparative Example C And D

Articles made according to Example 1 were tested according to the Bacterial Kill Assay and the Fungal Challenge Test and compared with articles of Comparative Examples C and D. The Bacterial Kill Assay was conducted for Salmonella and the data is presented in Table 5 and Table 6.

The two data sets (Tables 5 and 6) were collected because some of the initial data first collected for Comparative Example D (the 0X and 10X samples) were believed to be in error.

A separate Bacterial Kill Assay was conducted for *Staphylococcus Aureus* (ATCC 6538) as a control. This data is presented in Table 7.

Data for the Fungal Challenge Test is set forth in Table 8 for the standard ASTM G21-90 organisms. Table 9 includes Fungal Challenge data for articles treated with Penicillium. Zinc pyrithione is known to be relatively ineffective against this fungal species, and the data in Table 9 was collected as a control.

TABLE 1

Bacterial Kill Assay (Salmonella)

| Sample[1] | Day 0 Log change (Std. Dev.) | Day 1 (Std. Dev.) | Day 3 (Std. Dev.) | Day 7 (Std. Dev.) |
|---|---|---|---|---|
| Comp. Ex. A | | | | |
| 0×[2] | −0.4 (0.01) | +1.1 (0.04) | +1.0 (0.11) | +1.1 (0.04) |
| 10× | −0.4 (0.01) | +1.0 (0.02) | +0.7 (0.08) | +0.6 (0.08) |
| 100× | −0.5 (0.04) | +0.7 (0.19) | +0.7 (0.12) | +0.6 (0.03) |
| 200×[2] | −0.4 (0.02) | +1.1 (0.10) | +0.8 (0.09) | +1.0 (0.08) |
| 300× | −0.4 (0.03) | +1.2 (0.01) | +1.0 (0.11) | +1.0 (0.02) |
| 400× | −0.5 (0.03) | +1.0 (0.06) | +0.8 (0.08) | +0.8 (0.16) |
| Example 2 | | | | |
| 0× | −0.5 (0.04) | −4.8 (0.10) | −6.7 (0.00) | −6.7 (0.00) |
| 10× | −0.7 (0.12) | −4.3 (0.48) | −6.7 (0.00) | −6.7 (0.00) |
| 100× | −0.9 (0.15) | −4.7 (0.13) | −6.7 (0.00) | −6.7 (0.00) |
| 2 200× | −0.6 (0.14) | −5.6 (0.20) | −6.7 (0.00) | −6.7 (0.00) |
| 300× | −0.6 (0.20) | −6.2 (0.63) | −6.7 (0.00) | −6.7 (0.00) |
| 400× | −0.7 (0.07) | −6.3 (0.34) | −6.7 (0.00) | −6.7 (0.00) |
| Comp. Ex. B | | | | |
| 0×[2] | −0.2 (0.02) | −0.5 (0.03) | −1.3 (0.09) | −2.2 (0.27) |
| 10× | −0.3 (0.03) | +1.1 (0.04) | +1.0 (0.13) | +1.1 (0.07) |
| 100× | −0.3 (0.03) | +1.2 (0.04) | +0.9 (0.08) | +1.0 (0.14) |
| 200× | −0.3 (0.03) | +1.2 (0.07) | +1.2 (0.03) | +1.1 (0.06) |
| 300× | −0.3 (0.02) | +1.1 (0.09) | +0.9 (0.10) | +0.9 (0.10) |
| 400× | −0.2 (0.04) | +1.1 (0.05) | +0.8 (0.09) | +0.9 (0.04) |
| Example 4 | | | | |
| 0× | −0.1 (0.02) | −2.5 (0.20) | −5.0 (0.99) | −5.3 (0.66) |
| 10× | −0.2 (0.03) | −4.2 (0.13) | −6.9 (0.00) | −6.9 (0.00) |
| 100× | −0.2 (0.01) | −4.5 (0.25) | −6.9 (0.00) | −6.9 (0.00) |
| 200× | −0.1 (0.04) | −4.0 (0.07) | −6.8 (0.15) | −6.9 (0.00) |
| 300× | −0.1 (0.03) | −3.4 (0.03) | −6.9 (0.00) | −6.9 (0.00) |
| 400× | −0.1 (0.12) | −1.3 (1.851) | +1.2 (0.11) | +1.2 (0.04) |

1. "_x" indicates the number of times the substrate was rinsed and wrung prior to being tested.
2. Contamination believed to have been present in these samples.

TABLE 2

Bacterial Kill Assay (Pseudomonas)

| Sample[1] | Day 0 (Std. Dev.) | Day 1 (Std. Dev.) | Day 3 (Std. Dev.) | Day 7 (Std. Dev.) |
|---|---|---|---|---|
| Comp. Ex. A | | | | |
| 0×[2] | −0.6 (0.05) | +1.6 (0.05) | +1.7 (0.07) | +1.7 (0.06) |
| 10× | −0.6 (0.06) | +1.6 (0.09) | +1.6 (0.06) | +1.6 (0.05) |
| 100× | −0.5 (0.05) | +0.8 (0.99) | +1.7 (0.05) | +1.5 (0.14) |
| 200× | −0.6 (0.08) | +1.6 (0.08) | +1.7 (0.09) | +1.5 (0.03) |
| 300× | −0.7 (0.17) | +1.7 (0.05) | +1.7 (0.03) | +1.5 (0.05) |
| 400× | −0.7 (0.04) | +1.7 (0.04) | +1.8 (0.04) | +1.6 (0.05) |
| Example 2 | | | | |
| 0× | −0.9 (0.14) | −6.8 (0.00) | −6.8 (0.00) | −6.8 (0.00) |
| 10× | −0.8 (0.24) | −4.5 (1.48[1]) | −2.2 (2.88[1]) | +1.0 (0.58) |
| 100× | −1.2 (0.30) | −3.5 (0.45) | +0.3 (0.30) | +0.8 (0.10) |
| 200× | −1.7 (0.09) | −6.8 (0.00) | −6.8 (0.00) | −6.8 (0.00) |
| 300× | −2.1 (0.36) | −6.8 (0.00) | −6.8 (0.00) | −2.6 (4.86[1]) |
| 400× | −2.0 (0.07) | −5.8 (1.21) | −2.8 (0.52) | +0.5 (0.08) |
| Comp. Ex. B | | | | |
| 0× | −0.2 (0.04) | −1.1 (0.05) | −3.4 (0.16) | −2.8 (1.52) |
| 10× | −0.2 (0.03) | +1.5 (0.06) | +1.8 (0.09) | +2.2 (0.00) |
| 100× | −0.2 (0.06) | +1.7 (0.09) | +1.9 (0.03) | +2.0 (0.15) |
| 200× | −0.2 (0.06) | +1.6 (0.05) | +2.0 (0.14) | +2.2 (0.04) |
| 300× | −0.2 (0.04) | +1.5 (0.06) | +1.9 (0.06) | +2.1 (0.03) |
| 400× | −0.2 (0.03) | +1.6 (0.07) | +1.8 (0.03) | +1.8 (0.04) |
| Example 4 | | | | |
| 0× | −0.2 (0.08) | −0.4 (0.06) | −1.2 (0.04) | −3.6 (0.08) |

TABLE 2-continued

Bacterial Kill Assay (Pseudomonas)

| Sample[1] | Day 0 (Std. Dev.) | Day 1 (Std. Dev.) | Day 3 (Std. Dev.) | Day 7 (Std. Dev.) |
|---|---|---|---|---|
| 10× | −0.5 (0.06) | −3.7 (0.38) | −0.1 (1.73[1]) | +1.2 (0.05) |
| 100× | −0.6 (0.12) | −3.7 (0.14) | +1.1 (0.38) | +1.2 (0.05) |
| 200× | −0.6 (0.06) | −3.3 (0.17) | +0.9 (0.36) | +1.5 (0.02) |
| 300× | −0.5 (0.06) | −0.7 (1.08[1]) | +1.5 (0.09) | +1.6 (0.03) |
| 400× | −0.5 (0.07) | +1.3 (0.03) | +1.9 (0.32) | +1.8 (0.07) |

1. One of the two samples failed before the other.
2. "_x" indicates the number of times the substrate was rinsed and wrung out prior to testing

TABLE 3

Fungal Challenge (ASTM G21-90)

| | | EVALUATION[2] | | | |
|---|---|---|---|---|---|
| Sample[1] | Days to failure | Day 7 | Day 14 | Day 21 | Day 28 |
| C. Ex. A | | | | | |
| 0× | 4.0 (All failed) | 3.0 | 4.0 | 4.0 | 4.0 |
| 10× | 4.0 (All failed) | 3.3 | 4.0 | 4.0 | 4.0 |
| 100× | 4.0 (All failed) | 3.3 | 4.0 | 4.0 | 4.0 |
| 200× | 4.0 (All failed) | 3.5 | 4.0 | 4.0 | 4.0 |
| 300× | 4.0 (All failed) | 3.0 | 4.0 | 4.0 | 4.0 |
| 400× | 4.0 (All failed) | 3.0 | 4.0 | 4.0 | 4.0 |
| Example 2 | | | | | |
| 0× | 16.0 (2 of 4 failed) | 0.0 | 0.3 | 0.5 | 0.5 |
| 10× | 0.0 (None failed) | 0.0 | 0.0 | 0.0 | 0.0 |
| 100× | 10.5 (2 of 4 failed) | 0.3 | 0.5 | 0.5 | 0.5 |
| 200× | 7.0 (All failed) | 1.0 | 1.0 | 1.0 | 1.0 |
| 300× | 0.7 (3 of 4 failed) | 0.5 | 0.8 | 1.5 | 2.0 |
| 400× | 2.3 (All failed) | 0.0 | 1.0 | 3.0 | 3.8 |
| C. Ex. B | | | | | |
| 0× | 4.0 (All failed) | 2.0 | 4.0 | 4.0 | 4.0 |
| 10× | 4.0 (All failed) | 3.0 | 3.0 | 4.0 | 4.0 |
| 100× | 4.0 (All failed) | 3.0 | 4.0 | 4.0 | 4.0 |
| 200× | 4.0 (All failed) | 3.0 | 4.0 | 4.0 | 4.0 |
| 300× | 4.0 (All failed) | 3.0 | 3.5 | 4.0 | 4.0 |
| 400× | 4.0 (All failed) | 3.0 | 3.0 | 4.0 | 4.0 |
| Example 4 | | | | | |
| 0× | 18.5 (All failed) | 0.0 | 0.3 | 1.0 | 1.5 |
| 10× | 2.5 (All failed) | 0.5 | 1.0 | 1.3 | 1.5 |
| 100× | 9.0 (3 of 4 failed) | 0.3 | 1.0 | 2.5 | 2.0 |
| 200× | 5.5 (All failed) | 1.8 | 2.0 | 3.0 | 3.3 |
| 300× | 4.0 (All failed) | 2.0 | 2.5 | 3.5 | 3.8 |
| 400× | 4.0 (All failed) | 2.0 | 2.0 | 2.5 | 2.8 |

1. "_x" indicates the number of times the substrate was rinsed and wrung out prior to testing.
2. 0 = No growth observed
   1 = Trace growth, 1 to 10% coverage of sample surface by molds
   2 = Light growth, 10 to 30% coverage of sample surface by molds
   3 = Moderate growth, 30 to 60% coverage of sample surface by molds
   4 = Heavy growth, >60% coverage of sample surface by molds

TABLE 4

Fungal Challenge (ASTM G21-90 & Penicillium)

| | | EVALUATION[2] | | | |
|---|---|---|---|---|---|
| Sample[1] | Days to failure | Day 7 | Day 14 | Day 21 | Day 28 |
| C. Ex. A | | | | | |
| 0× | 4.0 (All failed) | 1.3 | 1.8 | 2.3 | 3.3 |
| 10× | 4.0 (All failed) | 1.0 | 1.0 | 1.0 | 2.0 |
| 100× | 4.0 (All failed) | 1.8 | 2.5 | 3.5 | 3.8 |
| 200× | 4.0 (All failed) | 1.5 | 1.8 | 2.3 | 3.0 |
| 300× | 4.0 (All failed) | 1.0 | 1.0 | 1.0 | 1.5 |
| 400× | 4.0 (All failed) | 1.3 | 1.3 | 1.3 | 2.3 |
| Example 2 | | | | | |
| 0× | 4.0 (3 of 4 failed) | 0.8 | 0.8 | 0.8 | 0.8 |
| 10× | 4.0 (All failed) | 1.0 | 1.0 | 1.0 | 1.0 |
| 00× | 4.0 (All failed) | 1.0 | 1.0 | 1.0 | 1.5 |
| 200× | 4.0 (All failed) | 1.0 | 1.0 | 1.0 | 2.0 |
| 300× | 4.0 (All failed) | 1.0 | 1.0 | 1.0 | 1.0 |
| 400× | 4.0 (All failed) | 1.0 | 1.0 | 1.0 | 1.0 |
| C. Ex. B | | | | | |
| 0× | 4.0 (All failed) | 1.0 | 2.0 | 3.0 | 3.0 |
| 10× | 4.0 (All failed) | 1.3 | 1.8 | 4.0 | 4.0 |
| 100× | 4.0 (All failed) | 2.0 | 2.0 | 4.0 | 4.0 |
| 200× | 4.0 (All failed) | 2.0 | 2.0 | 4.0 | 4.0 |
| 300× | 4.0 (All failed) | 1.8 | 2.3 | 4.0 | 4.0 |
| 400× | 4.0 (All failed) | 2.0 | 2.0 | 4.0 | 4.0 |
| Example 4 | | | | | |
| 0× | 4.0 (All failed) | 1.3 | 1.3 | 2.3 | 2.3 |
| 10× | 4.0 (All failed) | 1.0 | 1.0 | 1.0 | 1.5 |
| 100× | 4.0 (All failed) | 1.0 | 1.0 | 1.3 | 2.0 |
| 200× | 4.0 (All failed) | 1.0 | 1.0 | 2.0 | 2.0 |
| 300× | 4.0 (All failed) | 1.5 | 1.8 | 2.0 | 3.0 |
| 400× | 4.0 (All failed) | 1.5 | 1.5 | 1.5 | 3.0 |

1. "_x" indicates the number of times the substrate was rinsed and wrung out prior to testing.
2. 0 = No growth observed
   1 = Trace growth, 1 to 10% coverage of sample surface by molds
   2 = Light growth, 10 to 30% coverage of sample surface by molds
   3 = Moderate growth, 30 to 60% coverage of sample surface by molds
   4 = Heavy growth, >60% coverage of sample surface by molds

TABLE 5

Bacterial Kill Assay (Salmonella)

| Sample[1] | Day 0 (Std. Dev.) | Day 1 (Std. Dev.) | Day 3 (Std. Dev.) | Day 7 (Std. Dev.) |
|---|---|---|---|---|
| Comp. Ex. C | | | | |
| 0× | −0.3 (0.02) | +0.2 (0.48) | +1.1 (0.36) | +1.4 (0.14) |
| 10× | −0.5 (0.01) | +1.7 (0.04) | +1.9 (0.10) | +1.7 (0.01) |
| 100× | −0.5 (0.02) | +1.6 (0.05) | +1.5 (0.03) | +1.5 (0.07) |
| 200× | −0.4 (0.02) | +1.0 (0.06) | +1.1 (0.09) | +1.2 (0.06) |
| 300× | −0.5 (0.03) | +0.6 (0.01) | +1.1 (0.06) | +0.9 (0.08) |
| 400× | −0.5 (0.02) | +0.6 (0.10) | +1.3 (0.22) | +1.0 (0.12) |
| Example 1 | | | | |
| 0× | −0.2 (0.06) | −1.1 (0.10) | −5.9 (1.00) | −6.7 (0.00) |
| 10× | −0.4 (0.02) | −0.9 (0.17) | −3.9 (0.68) | −6.5 (0.00) |
| 100× | −0.6 (0.09) | −1.5 (0.08) | −6.4 (0.00) | −6.4 (0.00) |
| 200× | −0.8 (0.07) | −1.4 (0.51) | −6.1 (0.00) | −6.1 (0.00) |
| 300× | −0.7 (0.07) | −2.2 (0.06) | −6.2 (0.00) | −6.2 (0.00) |
| 400× | −0.9 (0.05) | −1.5 (0.20) | −6.1 (0.00) | −6.1 (0.00) |
| Comp. Ex. D | | | | |
| 0× | −0.3 (0.05) | −0.1 (0.07) | −1.5 (0.37) | −4.6 (0.00[2]) |
| 10× | −0.4 (0.02) | −0.4 (0.05) | −0.9 (0.08) | −4.5 (0.00) |
| 100× | −0.5 (0.03) | −2.2 (0.11) | −5.5 (0.13) | −6.4 (0.00) |
| 200× | −0.6 (0.04) | −1.7 (0.21) | −5.5 (0.28) | −6.2 (0.24) |

TABLE 5-continued

Bacterial Kill Assay (Salmonella)

| Sample[1] | Day 0 (Std. Dev.) | Day 1 (Std. Dev.) | Day 3 (Std. Dev.) | Day 7 (Std. Dev.) |
|---|---|---|---|---|
| 300x | −0.5 (0.07) | −0.7 (0.10) | −1.7 (0.64) | −1.7 (0.51) |
| 400x | −0.6 (0.06) | −0.6 (0.10) | −1.6 (0.11) | −1.5 (0.20) |

1. "_x" indicates the number of times the substrate was rinsed and wrung out prior to testing.
2. The lowest dilutions on these two samples were not plated. The lowest dilution plated was 1:100 and no organisms were recovered, so these two samples actually showed an average log reduction of >4.5/4.6.

TABLE 6

Bacterial Kill Assay (Salmonella)

| Sample[1] | Day 0 (Std. Dev.) | Day 1 (Std. Dev.) | Day 3 (Std. Dev.) | Day 7 (Std. Dev.) |
|---|---|---|---|---|
| Comp. Ex. C | | | | |
| 0x | −0.0 (0.02) | +1.4 (0.05) | +1.8 (0.13) | +1.7 (0.05) |
| 10x | −0.2 (0.04) | +1.9 (0.03) | +2.0 (0.03) | +2.0 (0.01) |
| 100x | −0.2 (0.03) | +1.7 (0.07) | +1.9 (0.07) | +1.9 (0.04) |
| 200x | −0.3 (0.07) | +1.7 (0.06) | +1.8 (0.04) | +1.9 (0.02) |
| 300x | −0.2 (0.07) | +1.2 (0.11) | +1.6 (0.03) | +1.6 (0.01) |
| 400x | −0.2 (0.01) | +1.0 (0.08) | +1.5 (0.05) | +1.6 (0.11) |
| Example 1 | | | | |
| 0x | +0.0 (0.04) | −0.9 (0.08) | −6.3 (0.58) | −6.8 (0.00) |
| 10x | −0.3 (0.04) | −0.9 (0.06) | −1.7 (0.24) | −6.5 (0.00) |
| 100x | −0.4 (0.07) | −0.5 (0.02) | −2.2 (0.20) | −6.4 (0.00) |
| 200x | −0.2 (0.03) | −0.9 (0.22) | −3.2 (0.10) | −6.5 (0.00) |
| 300x | −0.3 (0.05) | −1.0 (0.03) | −3.2 (0.59) | −6.5 (0.00) |
| 400x | −0.4 (0.04) | −0.8 (0.11) | −2.8 (0.11) | −6.4 (0.00) |
| Comp. Ex. D | | | | |
| 0x | −0.1 (0.02) | −0.2 (0.04) | −0.5 (0.11) | −3.5 (0.58) |
| 10x | −0.2 (0.05) | −0.3 (0.03) | −0.8 (0.10) | −4.0 (0.42) |
| 100x | −0.4 (0.03) | −0.7 (0.12) | −2.0 (0.15) | −6.4 (0.00) |
| 200x | −0.4 (0.02) | −1.1 (0.24) | −3.3 (0.41) | −6.4 (0.00) |
| 300x | −0.4 (0.02) | −0.9 (0.06) | −3.1 (0.36) | −6.4 (0.00) |
| 400x | −0.3 (0.04) | −0.7 (0.05) | −3.1 (0.26) | −6.2 (0.27) |

1. "_x" indicates the number of times the substrate was rinsed and wrung out prior to testing.

TABLE 7

Bacterial Kill Assay (Staphylococcus Aureus)

| Sample[1] | Day 0 (Std. Dev.) | Day 1 (Std. Dev.) | Day 3 (Std. Dev.) | Day 7 (Std. Dev.) |
|---|---|---|---|---|
| Comp. Ex. C | | | | |
| 0x | −7.1 (0.00) | −7.1 (0.00) | −7.1 (0.00) | −7.1 (0.00) |
| 10x | −1.6 (0.19) | −5.6 (0.00) | −5.6 (0.00) | −5.6 (0.00) |
| 100x | −1.2 (0.09) | −3.4 (0.09) | −4.3 (0.19) | −5.8 (0.17) |
| 200x | −0.5 (0.05) | −1.2 (0.06) | −1.9 (0.03) | −3.4 (0.16) |
| 300x | −0.5 (0.03) | −0.3 (0.02) | −0.4 (0.15) | −1.2 (0.14) |
| 400x | −0.5 (0.08) | −0.3 (0.09) | −0.4 (0.08) | −1.4 (0.21) |
| Example 1 | | | | |
| 0x | −0.9 (0.19) | −6.2 (0.00) | −6.2 (0.00) | −6.2 (0.00) |
| 10x | −0.8 (0.17) | −6.4 (0.00) | −6.4 (0.00) | −6.4 (0.00) |
| 100x | −0.3 (0.06) | −2.7 (0.55) | −6.9 (0.00) | −6.9 (0.00) |
| 200x | −0.3 (0.08) | −2.3 (0.02) | −6.8 (0.15) | −6.8 (0.00) |
| 300x | −0.3 (0.04) | −1.8 (0.10) | −6.4 (0.52) | −6.8 (0.15) |
| 400x | −0.3 (0.06) | −2.0 (0.04) | −6.4 (0.29) | −6.8 (0.00) |
| Comp. Ex. D | | | | |
| 0x | −0.6 (0.29) | −6.5 (0.00) | −6.5 (0.00) | −6.5 (0.00) |
| 10x | −0.3 (0.06) | −6.7 (0.00) | −6.7 (0.00) | −6.7 (0.00) |
| 100x | −0.2 (0.03) | −5.2 (0.29) | −6.8 (0.00) | −6.8 (0.00) |
| 200x | −0.1 (0.01) | −2.8 (0.21) | −6.9 (0.00) | −6.9 (0.00) |
| 300x | −0.2 (0.03) | −2.8 (0.06) | −6.8 (0.15) | −6.9 (0.00) |
| 400x | −0.1 (0.04) | −1.3 (0.47) | −4.0 (0.62) | −6.9 (0.00) |

1. "_x" indicates the number of times the substrate was rinsed and wrung out prior to testing.

TABLE 8

Fungal Challenge (ASTM G21-90)

| Sample[1] | Days to failure | EVALUATION[2] Day 7 | Day 14 | Day 21 | Day 28 |
|---|---|---|---|---|---|
| C. Ex. C | | | | | |
| 0x | 2.0 (All failed) | 3.0 | 4.0 | 4.0 | 4.0 |
| 10x | 1.0 (All failed) | 3.0 | 4.0 | 4.0 | 4.0 |
| 100x | 1.5 (All failed) | 3.0 | 4.0 | 4.0 | 4.0 |
| 200x | 2.0 (All failed) | 3.0 | 4.0 | 4.0 | 4.0 |
| 300x | 2.0 (All failed) | 3.0 | 4.0 | 4.0 | 4.0 |
| 400x | 2.0 (All failed) | 3.0 | 4.0 | 4.0 | 4.0 |
| Example 1 | | | | | |
| 0x | No failures | 0.0 | 0.0 | 0.0 | 0.0 |
| 10x | No failures | 0.0 | 0.0 | 0.0 | 0.0 |
| 00x | No failures | 0.0 | 0.0 | 0.0 | 0.0 |
| 200x | No failures | 0.0 | 0.0 | 0.0 | 0.0 |
| 300x | No failures | 0.0 | 0.0 | 0.0 | 0.0 |
| 400x | No failures | 0.0 | 0.0 | 0.0 | 0.0 |
| C. Ex. D | | | | | |
| 0x | No failures | 0.0 | 0.0 | 0.0 | 0.0 |
| 10x | No failures | 0.0 | 0.0 | 0.0 | 0.0 |
| 100x | 12.0 (All failed) | 0.3 | 0.8 | 2.0 | 3.5 |
| 200x | 3.5 (All failed) | 1.5 | 2.5 | 3.3 | 3.8 |
| 300x | 5.0 (All failed) | 0.8 | 1.8 | 2.3 | 3.0 |
| 400x | 5.3 (All failed) | 0.8 | 1.8 | 2.3 | 3.0 |

1. "_x" indicates the number of times the substrate was rinsed and wrung out prior to testing.
2. 0 = No growth observed
1 = Trace growth, 1 to 10% coverage of sample surface by molds
2 = Light growth, 10 to 30% coverage of sample surface by molds
3 = Moderate growth, 30 to 60% coverage of same surface by molds
4 = Heavy growth, >60% coverage of sample surface by molds

TABLE 9

Fungal Challenge (Penicillium)

| Sample[1] | Days to failure | EVALUATION[2] Day 7 | Day 14 | Day 21 | Day 28 |
|---|---|---|---|---|---|
| C. Ex. C | | | | | |
| 0x | 2.0 (All failed) | 1.0 | 2.0 | 2.0 | 2.0 |
| 10x | 2.0 (All failed) | 2.8 | 3.8 | 3.8 | 3.8 |
| 100x | 2.0 (All failed) | 1.0 | 2.0 | 2.0 | 2.3 |
| 200x | 2.0 (All failed) | 1.8 | 2.8 | 3.0 | 3.0 |
| 300x | 2.0 (All failed) | 1.0 | 2.0 | 2.3 | 2.3 |
| 400x | 2.0 (All failed) | 1.3 | 2.3 | 2.3 | 2.3 |
| Example 1 | | | | | |
| 0x | 2.0 (All failed) | 1.0 | 2.0 | 2.0 | 2.0 |
| 10x | 2.5 (All failed) | 1.0 | 2.0 | 2.0 | 2.0 |
| 100x | 2.0 (All failed) | 1.0 | 2.0 | 2.0 | 2.0 |
| 200x | 2.0 (All failed) | 1.0 | 2.0 | 2.0 | 2.0 |

TABLE 9-continued

Fungal Challenge (Penicillium)

| | | EVALUATION[2] | | | |
|---|---|---|---|---|---|
| Sample[1] | Days to failure | Day 7 | Day 14 | Day 21 | Day 28 |
| 300× | 2.0 (All failed) | 1.0 | 2.0 | 2.0 | 2.0 |
| 400× | 2.0 (All failed) | 1.0 | 2.0 | 2.0 | 2.0 |
| C. Ex. D | | | | | |
| 0× | 2.0 (All failed) | 1.0 | 2.0 | 2.0 | 2.0 |
| 10× | 2.0 (All failed) | 1.0 | 2.0 | 2.0 | 2.0 |
| 100× | 2.0 (All failed) | 1.0 | 2.0 | 2.0 | 2.0 |
| 200× | 2.0 (All failed) | 1.0 | 2.0 | 2.0 | 2.0 |
| 300× | 2.0 (All failed) | 1.0 | 2.0 | 2.0 | 2.0 |
| 400× | 2.0 (All failed) | 1.0 | 2.0 | 2.0 | 2.0 |

1. "_x" indicates the number of times the substrate was rinsed and wrung out prior to testing.
2. 0 = No growth observed
   1 = Trace growth, 1 to 10% coverage of sample surface by molds
   2 = Light growth, 10 to 30% coverage of sample surface by molds
   3 = Moderate growth, 30 to 60% coverage of sample surface by molds
   4 = Heavy growth, >60% coverage of sample surface by molds

Example 10–16

Nonwoven wipes were prepared from, crosslapped, and needle punched nonwoven webs comprised of 20% rayon fibers (fiber type "18552", 1.5 denier×51 mm, Courtalds Chemical Company, England) amd 80% poly(vinyl alcohol) fibers (fiber type "VPB 202", 2.0 denier×51 mm, Kuraray KK, Japan) with a basis weight of 158 g/m$^2$ and a thickness of 2.3 mm.

A coating solution was prepared to contain 45.5 g of a 10% aqueous solution of poly(vinyl alcohol) ("R1130" from Kuraray KK, Japan), 2.25 g crosslinker ("Tyzor 131" from DuPont Company, Wilmington, Del.), 0.22 g colloidal silica ("Nalco 8676" from Nalco Chemical Company, Naperville, Ill.), 1.0 g Orcobrite RED BRYN 6002 pigment (Organic Dyestuffs Corporation, Concord, N.C.), and 154 g deionized water.

An Ion/Polymer Solution was made by dissolving 15 g of 60 mesh chitosan (Vanson, Redmond, Wash.) in a 5% solution of glacial acetic acid, followed by reaction, without gelation, of the chitosan with an excess of zinc acetate (Aldrich Chemical Company, Milwaukee, Wis.). A measure amount of this zinc-chitosan solution was added to the foregoing coating solution in order to achieve the desired chitosan levels in the dried resin.

A 30.5 cm by 38.1 cm piece of the blended nonwoven web was hand coated with the coating solution, dried at 65.5° C., and cured at 162.7° C. for fifteen (15) minutes. Upon completion of the cure, the sample was rinsed by hand and reacted with a 10% solution of sodium pyrithione for thirty (30) minutes. The articles were subjected to a final hand rinsing using warm tap water. The articles of Examples 11, 13 and 15 were subjected to a final rinse by soaking the articles for 3 hours in water maintained at approximately 66° C. After the final rinse, each of the articles was tested for pyrithione attachment and for antimicrobial (antifungal) efficacy according to the Fungal Challenge Test. Data for this testing are reported below in Table 10 along with a description for each of the wipes made according to the described procedure. The description includes an indication of the chitosan level in the dry resin.

Comparative Examples E–H

Additional articles were prepared for use as Comparative Examples in the testing reported below. The articles were prepared as in Examples 10–15 except that the webs were not treated with sodium pyrithione. Comparative Example E was prepared to comprise 0.7 wt % chitosan, Comparative Example F was prepared to comprise 1.4 wt % chitosan, and Comparative Example G was prepared to comprise 1.8 wt % chitosan. Comparative Example H was prepared without added chitosan in the coating solution, but powdered chitosan was applied by hand to the finished article. Test data are set forth in Table 10.

Example 17–25

Acrylic latex-based wipes were prepared for Examples 17–23 and Example 25 from a carded, crosslapped, and needlepunched nonwoven web comprised of 20% rayon fibers (18552, 1.5 denier×51 mm, Courtalds Chemical Company, England) and 80% poly(vinyl alcohol) fibers (VPB 202, 2.0 denier×51 mm, Kuraray KK, Japan) with a basis weight of 158 g/m$^2$ and a thickness of 2.3 mm.

A coating solution was prepared to contain 4.8 g of a 55.4% aqueous dispersion of a styrenated acrylic latex ("T278", B. F. Goodrich Company, Cleveland, Ohio), 0.52 g crosslinker ("Primid XL-552" from Rohm and Haas Company, Philadelphia, Pa.), 0.25 g Orcobrite RED BRYN 6002 pigment (Organic Dyestuffs Corporation, Concord, N.C.), and 29.6 g deionized water.

An ion/polymer solution was prepared by dissolving 15 g of 60 mesh chitosan (Vanson, Redmond, Wash.) in a 5% solution of glacial acetic acid, followed by reaction, without gelation, of the chitosan with an excess of zinc acetate (Aldrich Chemical Company, Milwaukee, Wis.). A measured amount of the 5% zinc-chitosan solution was added to the above coating solution to achieve the desired level of the chitosan in the dried resin of the finished article.

A 19 cm by 21 cm piece of the blended nonwoven web was hand coated with the coating solution, dried at 65.5° C., and cured at 107.2° C. for fifteen (15) minutes. Upon completion of the cure, the sample was rinsed and reacted with a 10% solution of sodium pyrithione for thirty (30) minutes. Upon a final rinsing, some of the wipes were immediately tested for pyrithione attachment and antimicrobial (antifungal) efficacy according to the Fungal Challenge Test.

The article of Example 24 was a PVA-based wipe made according to the general procedure of Examples 10–16, treated with zinc-chitosan-pyrithione and having a chitosan concentration in the dried coating of 1.5% by weight.

Comparative Examples I–L

Articles were prepared for use as Comparative Examples. Articles of Comparative Examples I and J were prepared as in Examples 17–23 and 25. Articles of Comparative Examples K and L were prepared as in Examples 10–16. Some of the articles were treated with added zinc-chitosan in the coating solution without a subsequent treatment of pyrithione. Other articles were made with no zinc-chitosan in the coating solution and were subsequently treated by the hand application of a specified amount of dry chitosan powder. A description of the articles and test data for the Fungal Challenge are presented in Table 11.

Example 26 and 27

Hand pads were prepared by dip-coating commercially available non-woven scouring products. Example 26 was a "Scotch-Brite" LP-96 hand pad available from Minnesota Mining and Manufacturing Company, St. Paul Minn. and Example 27 was a "Scotch-Brite" LP-98 hand pad, also available from Minnesota Mining and Manufacturing Company. The pads were treated with a solution of zinc-chitosan, prepared as described Example 17. Excess solution was removed using a mechanical wringer. The article was then dried at 120° F. and placed in a plastic bag with approximately 250 ml of a 2000 ppm sodium pyrithione solution. The article was left to react for thirty (30) minutes at room temperature. Upon expiration of the thirty minutes, the article was rinsed in tap water and dried again at 120° F. for several hours before being tested for pyrithione uptake and microbiological efficacy.

These samples were evaluated for antifungal efficacy according to the standard test procedure ASTM G21-90 for twenty-eight (28) days. Both Example 27 and Example 28 were evaluated with duplicate ratings of 1.5 for Example 27 and duplicate ratings of 1.0 for Example 28. A rating of 1 indicated trace growth observed, with 1–10% of the sample surface showing some fungal growth. A rating of 2 indicates light growth and 10–30% sample coverage.

Examples 10–16 and Comparative Examples E–H

Article made according to Examples 10–16 and Comparative Examples E–H were tested according to the Fungal Challenge using the organisms of ASTM G21-90. Data was collected for duplicate samples at 28 days following inoculation with the test organisms. The data is presented in Table 10.

TABLE 10

Fungal Challenge Test Results

| Example | Description | Rating at 28 Days |
|---|---|---|
| Ex. 10 | 0.7% Chitosan. | 0,0 |
| C. Ex. E | 0.7% Chitosan. | 4,4 |
| Ex. 11 | 0.7% Chitosan. - (rinsed at 66° C. for 3 hrs). | 1,1 |
| C. Ex. F | 1.4% Chitosan | 4,4 |
| Ex. 12 | 1.4% Chitosan. | 0,0 |
| Ex. 13 | 1.4% Chitosan. - (rinsed at 66° C. for 3 hrs). | 1,0 |
| Ex. 14 | 1.8% Chitosan. | 0,0 |
| C. Ex. G | 1.8% Chitosan | 4,4 |
| Ex. 15 | 1.8% Chitosan. (rinsed at 66° C. for 3 hrs). | 0,0 |
| Ex. 16 | 1.5% Chitosan. | 0,0 |
| C. Ex. H | Sprinkled with 0.6 grams dry chitosan. | 0,0 |

The data show that incorporation of the zinc-chitosan-pyrithione complex into a wipe resin formulation provides excellent protection against fungal growth. Chitosan alone (e.g., without pyrithione), is believed to be insufficient protection against fungal growth. The good results for Comparative Example H are inconsistent with other data for samples treated with chitosan but without pyrithione. The inventive process provides a wipe with an antimicrobial treatment durable enough to withstand hand rinsing.

Examples 17–25 and Comparative Examples I–L

Articles made according to Examples 17–25 and Comparative Examples I–L were tested using the Fungal Challenge with organisms required by standard test procedure ASTM G21-90. Data was collected in duplicate after 28 days following inoculation with the test organisms.

The articles of Examples 21–25 and Comparative Examples K and L were first subjected to a wash cycle in a washing machine with rinse temperatures ranging from 40° C. to 95° C. These articles were laundered in a commercially available wash machine (available under the trade designation "ASKO 20004" from ASKO USA, Inc. of Richardson, Tex.), a front-loading unit capable of washing clothes at water temperatures from 20° C. to 95° C.

Fungal Challenge testing was conducted for these articles after washing. The test data is set forth in Table 11 along with descriptive information for each of the tested articles, including the level of chitosan in the dried resin.

TABLE 11

Fungal Challenge Test Results

| Sample | Description | Rating at 28 days |
|---|---|---|
| C. Ex. I | Sprinkled with 0.5 grams dry chitosan. | 3,3 |
| Ex. 17 | 1.5% chitosan in the dried coating. | 0,0 |
| Ex. 18 | 2.0% chitosan in the dried coating. | 0,0 |
| Ex. 19 | 2.0% chitosan in the dried coating. | 0,0 |
| Ex. 20 | 2.0% chitosan in the dried coating. | 0,0 |
| C. Ex. J | 2.0% chitosan in the dried coating. | 4,4 |
| Ex. 21 | 2.0% chitosan in the dried coating. Laundered once at 40° C. | 0,0 |
| Ex. 22 | 2.0% chitosan in the dried coating. Laundered once at 60° C. | 4,4 |
| Ex. 23 | 2.0% chitosan in the dried coating. Laundered once at 95° C. | 4,4 |
| Ex. 24 | PVA-based wipe (1.5% chitosan in the dried coating). Laundered once at at 95° C. | 4,4 |
| Ex. 25 | 1.5% chitosan in the dried coating. Laundered once at 95° C. | 4,4 |
| C. Ex. K | PVA-based wipe sprinkled with 0.6 grams dry chitosan and laundered once at 95° C. | 4,4 |
| C. Ex. L | PVA-based wipe sprinkled with 0.6 grams dry chitosan and laundered twice at 95° C. | 4,4 |

The above results show that articles made according to the present invention have excellent protection against fungal growth. The Fungal Challenge data show that zinc-chitosan alone does not provide sufficient protection against fungal growth. Additionally, the inventive method provides articles with an antimicrobial treatment durable enough to withstand rinse/wash cycles at moderate temperatures (e.g., 40° C.). Durability for articles subjected to rinsing at more extreme temperatures (e.g., 60–95° C.), however, was poor.

While the foregoing disclosure describes the preferred embodiment of the invention, changes and modifications to the disclosed embodiment may be possible to those skilled in the art without departing from the true spirit and scope of the invention, as set forth in the appended claims.

What is claimed is:

1. A method of making an anti-microbial article comprising:
   providing a substrate;
   forming a solution comprising a chelating polymer and a metal ion;
   depositing the solution on the substrate;
   drying the substrate to form a coated substrate; and
   adding a potentiator to the coated substrate to form the antimicrobial article.

2. The method of claim 1 wherein forming a solution comprising a chelating polymer and a metal ion comprises (A) selecting a chelating polymer from the group consisting of polyglucosamines, ethylene acrylic acid copolymers, polycarboxylic acids, and polyamines, (B) dissolving the chelating polymer in acid to form an acidic solution, (C) preparing an aqueous solution of the metal ion, and (D) combining the aqueous solution of the metal ion and the acidic solution.

3. The method of claim 2 wherein the polyglucosamine is chitosan.

4. The method of claim 2 wherein preparing an aqueous solution of the metal ion comprises selecting a salt of the metal ion and dissolving the salt in water.

5. The method of claim 4 wherein the metal ion is selected from the group consisting of zinc, zirconium, iron and copper.

6. The method of claim 1 wherein the solution is deposited on the substrate by dipping the substrate in the solution and wringing excess solution from the substrate after dipping.

7. The method of claim 1 wherein the substrate is dried in an oven at a temperature within the range between 105° C. and 120° C.

8. The method of claim 1 wherein adding a potentiator to the coated substrate is accomplished by dissolving the potentiator in water to provide a potentiator solution, treating the coated substrate with the potentiator solution, drying the substrate to provide the finished anti-microbial article.

9. The method of claim 1 wherein the potentiator is selected from the group consisting of alkyl dithiocarbamates, thiazoles, imidazoles, pyrithione or mixtures thereof.

10. A method of for the treatment of a substrate to provide an antimicrobial article, the method comprising:

depositing a solution on the substrate to form a coated substrate, the solution comprising a chelating polymer and a metal ion;

drying the coated substrate;

adding a potentiator to the dried coated substrate to form the antimicrobial article.

11. The method of claim 10 further comprising forming the solution comprising a chelating polymer and a metal ion by (A) selecting a chelating polymer from the group consisting of polyglucosamine, ethylene acrylic acid copolymer, polycarboxylic acid, and polyamine, (B) dissolving the chelating polymer in acid to form an acidic solution, (C) preparing an aqueous solution of the metal ion, and (D) combining the aqueous solution of the metal ion and the acidic solution.

12. The method of claim 11 wherein the polyglucosamine is chitosan.

13. The method of claim 11 wherein preparing an aqueous solution of the metal ion comprises selecting a salt of the metal ion and dissolving the salt in water.

14. The method of claim 13 wherein the metal ion is selected from the group consisting of zinc, zirconium, iron and copper.

15. The method of claim 10 wherein the solution is deposited on the substrate by dipping the substrate in the solution and wringing excess solution from the substrate after dipping.

16. The method of claim 10 wherein the substrate is dried in an oven at a temperature within the range between 105° C. and 120° C.

17. The method of claim 10 wherein adding a potentiator to the coated substrate is accomplished by dissolving the potentiator in water to provide a potentiator solution, treating the coated substrate with the potentiator solution, drying the substrate to provide the finished anti-microbial article.

18. The method of claim 10 wherein the potentiator is selected from the group consisting of alkyl dithiocarbamates, thiazoles, imidazoles, pyrithione or mixtures thereof.

* * * * *

UNITED STATES PATENT AND TRADEMARK OFFICE
CERTIFICATE OF CORRECTION

PATENT NO. : 6,042,877
DATED : March 28, 2000
INVENTOR(S) : R. Lyon and Michael M. Rock, Jr.

It is certified that error appears in the above-identified patent and that said Letters Patent is hereby corrected as shown below:

First Page References Cited, after "8-1334778 5/1996 Japan", please insert OTHER PUBLICATIONS Vanson Chemical Company, 'Chitin and Chitosan - General Properties and Applications,"", Pages 1-7 (undated document, available at least as early as June 25, 1992)--.

Col. 12, line 34, Table 1, last line, "1.3(1.851)" should read -- $1.3(1.85^1)$ --.

Col. 12, line 57, Table 2, Example 2, Row 400X, "-5.8(1.21)" should read-- $-508 (1.21^1)$ --.

Col. 13, line 34, Table 3, Example 2, Row 300X, "0.7(3 of 4 failed)" should read --10.7 (3 of 4 failed)--.

Col. 13, line 45, Table 3, Example 4, Row 10X, "2.5(all failed)" should read --12.5 (all failed)--.

Col. 14, line 17, Table 4, Example 2, Row 100X, "00X" should read --100X--.

Col. 16, line 32, Table 8, Example 1, Row 100X, "00X" should read --100X--

Signed and Sealed this

Fifth Day of June, 2001

Attest:

*Attesting Officer*

NICHOLAS P. GODICI
*Acting Director of the United States Patent and Trademark Office*